United States Patent [19]

de France

[11] Patent Number: 4,573,195
[45] Date of Patent: Feb. 25, 1986

[54] SYSTEM FOR THE AUTOMATIC OBSERVATION AND QUANTIFICATION OF PHENOMENA CAPABLE OF BEING DETECTED BY FLUORESCENCE

[76] Inventor: Henri G. de France, 6, rue du Dr. Brouardel, 75016 Paris, France

[21] Appl. No.: 528,007

[22] Filed: Aug. 31, 1983

[30] Foreign Application Priority Data

Sep. 3, 1982 [FR] France .................. 82 15054

[51] Int. Cl.⁴ .................. G06K 9/00; H04N 5/52
[52] U.S. Cl. .................................... 382/6; 356/39; 358/174; 358/223
[58] Field of Search .................. 358/223, 174, 107; 382/6; 356/39; 364/414

[56] References Cited

U.S. PATENT DOCUMENTS

| 3,131,257 | 4/1964 | Wallace | 358/223 |
| 3,389,221 | 6/1968 | Macdonald | 358/174 |
| 3,499,109 | 3/1970 | Kihara et al. | 358/223 |
| 3,715,490 | 2/1973 | Okada | 358/223 |
| 3,950,610 | 4/1976 | Hopkins | 382/6 |
| 4,048,616 | 9/1977 | Hart et al. | 382/6 |
| 4,207,554 | 6/1980 | Resnick et al. | 382/6 |
| 4,437,118 | 3/1984 | Singer | 358/223 |

Primary Examiner—Leo H. Boudreau
Assistant Examiner—Joseph Mancuso
Attorney, Agent, or Firm—Sughrue, Mion, Zinn Macpeak & Seas

[57] ABSTRACT

A system for the automatic observation and quantification of phenomena capable of being detected by fluorescence and appearing in a localized zone (8), the system comprising a source of radiation (2), optionally associated with an excitation filter (5) to send on the localized zone (8) an excitation radiation capable of producing the fluorescence, optical observation means (7) of the localized zone (8) and at least one filter (12) intended to block the excitation radiation and arranged in the path of the luminous radiation of fluorescence emanating from the localized zone (8). In accordance with the invention, the localized zone (8) is observed by a picture-taking tube (17) and through colored filters or windows on a disc (18) intercepting beam 11. The sucessive colored images are memorized and then read simultaneously.

13 Claims, 12 Drawing Figures

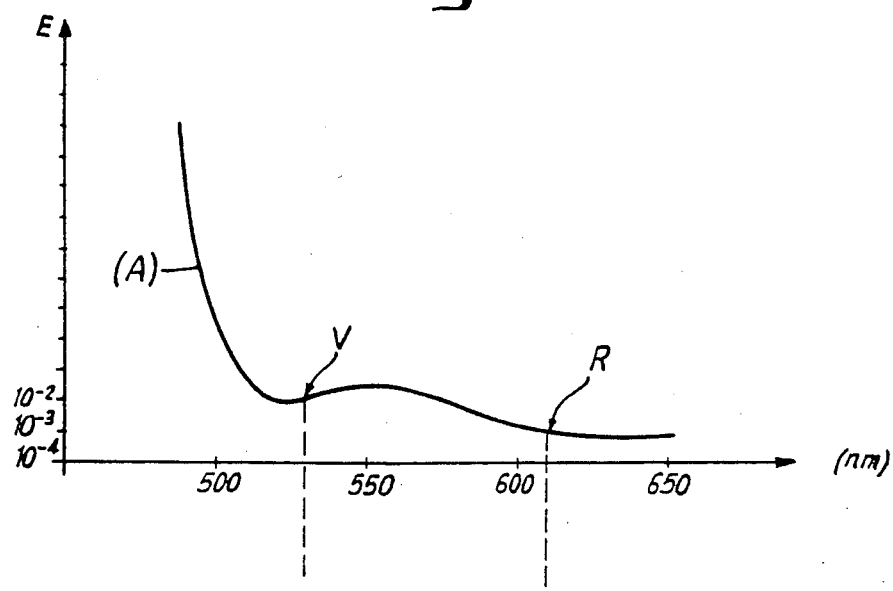
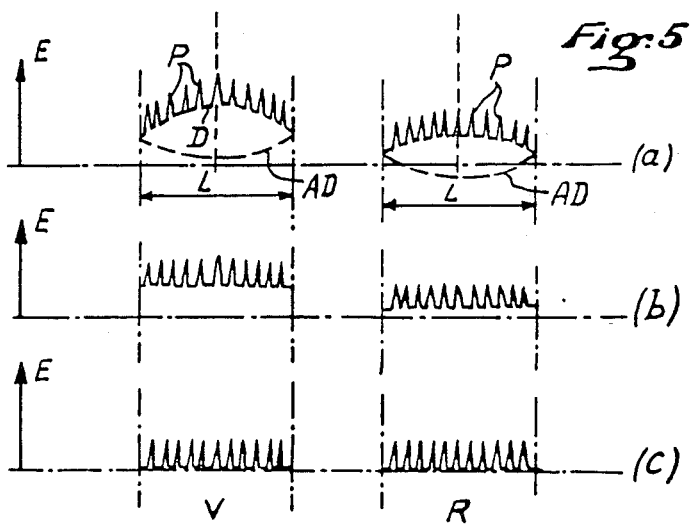

SYSTEM FOR THE AUTOMATIC OBSERVATION AND QUANTIFICATION OF PHENOMENA CAPABLE OF BEING DETECTED BY FLUORESCENCE

The present invention relates to a system providing for the observation and automatic quantification of phenomena capable of being detected by the emission of fluorescence, the fluorescence being either spontaneous or induced. While not exclusively, the invention is particularly applicable to immunofluorescence-that is, to the study of the immunological reactions of living organisms by marking reaction products with one or more fluorescent substances which render the reaction visible-and, for purposes of explanation, the invention will be described below more especially within the framework of that particular application, which should not be considered as limiting the scope of the present invention.

It is known that fluorescence is the property of certain substances of emitting photons in response to the reception of visible or invisible radiation. With the exception of the so-called resonance fluorescence phenomenon, caused by the loss of energy between the absorption and the emission of radiation, fluorescence photons are less energetic than the incident radiation photons, and their wavelength, is therefore, higher.

During the bombardment of molecules capable of fluorescence with a radiation source having an adequate wavelength, electrons from these molecules leave their normal stable orbits to pass onto outer orbits which correspond to higher energy levels, by forming excited singlets. When de-energization occurs, the electrons fall back into their stable orbits, thereby emitting fluorescence photons.

The life span of this fluorescence is very short, on the order of a nanosecond, although it is variable in accordance with the nature and the physical state of the excited molecules. Even with continuous irradiation, the phenomenon of fluorescence decreases exponentially as a function of time. Moreover, the quantum yield of fluorescence is low, for example equal to 3% for the fluorescence of chlorophyl, such that the intensity of the fluorescence, which nevertheless varies as a function of the intensity of the energization source, of the concentration, of the pH, of the presence of impurities and of the nature of the excited molecules, is also low. It can therefore, easily be seen that, due to its transient nature and its continuously decreasing low intensity, the phenomenon of fluorescence is particularly difficult to observe and to quantify.

Numerous organic compounds, even synthesized, are spontaneously fluorescent. The same applies to numerous plants, animals, insects, etc. Moreover, it is known to manufacture fluorescent dyes, such as fluorescein isothiocyanate (ITCF) which emits in green, tetramethyl rhodamine isothiocyanate which emits in red, aminonaphthalene sulfonyl chloride which emits in yellow, "Evans blue" which is intended to screen out certain spontaneous fluorescences when they introduce a nuisance and which emits in red, etc.

The fluorescent dye which is currently the most used is ITCF. It has to be excited by a source whose maximum wavelength approaches 495 nm in the blue and which re-emits in green with a maximum at 520 nm, the emission extending, however, beyond 600 nm, that is, in the red.

In addition, it is known that the immunological reactions which occur in a living organism result from the meeting of a substance which, in principle, is foreign to the organism, known as an antigen, and an antibody or immunoglobulin, produced by the organism to oppose the antigen.

The reactions between antibodies and antigens may be carried out by precipitation or by agglutination and such agglutination is already used to quantify antibody-antigen reactions. However, all antibodies are not agglutinants and, for practical reasons, it appeared interesting to employ other techniques for quantification of antibody-antigen reactions.

Thus, A. H. Coons has already proposed a technique known as immunofluorescence, in accordance with which antibodies (and sometimes antigens) are bonded, directly or indirectly, to a fluorescent body, most frequently the ITCF mentioned above, such that the antibody-antigen reaction is rendered fluorescent and therefore visible, when the antibodies are fixed on the antigens. Such a technique is sensitive and rapid and does not necessitate placing organisms in a culture. In the direct process, an immunoserum to which a fluorescent dye has been added is applied on the antigen. In the indirect process, the fluorescent body is fixed on an "antibody" or antiglobulin, which has been prepared in advance and is capable of itself being fixed on the antibody which is to be studied.

On the sections of tissue, the immunofluorescence reaction permits the cells of the type to be studied to be clearly shown in relation to others which will not be rendered fluorescent. Marking by immunofluorescence is less complicated than radioimmunological marking.

To employ such a technique of immunofluorescence for a reaction or a phenomenon appearing in a localized zone (generally a glass slide, a cell from a plate of cells, etc.), a system has already been employed which comprises a source of radiation, possibly associated with at least one excitation filter, so as to send onto said localized zone excitation radiation likely to produce the fluorescence, optical means associated with the eye, in order to observe the localized zone, and at least one blocking filter so that only the emission of fluorescence coming from the localized zone may reach the eye. In the case of immunofluorescence using ITCF, the source of radiation is for example a mercury vapor arc lamp of the HBO 100 type, with considerable luminance, on the order of $1.5 \times 10^9$ cd/m$^2$ and emitting in blue.

Excitation filters, arranged downstream of the radiation source, select the radiation necessary to produce fluorescence, while blocking filters, preferably arranged between the localized zone and the eye, eliminate radiation not relating to the phenomenon of fluorescence. Since the maximum wavelengths of the excitation radiation and of the emission of the fluorescence are close to each other, the choice of excitation filters and blocking filters is extremely delicate in practice.

Optical observation means are always composed of a microscope which is specially adapted for the technique of immunofluorescence and, therefore, sophisticated, high performing, delicate, costly and exacting for the operator. This microscope contains, downstream from the source of radiation and the excitation filters, a dichroic mirror enabling the excitation radiation to be sent towards the localized zone and allowing the emission of fluorescence to pass towards the eye of the observer. In addition, the microscope contains a stage carring a plurality of localized zones, controls enabling the stage to be moved under one or several various magnification objective lenses and an eyepiece. The objective lens(es) produce a real image of the object being observed, whilst the eyepiece provides a virtual magnified image.

As the controls of the stage are actuated, the eye sees passing by the eyepiece a part of the object (difficult to situate) after appropriate individual focusing has been carried out. Thus, several people cannot conveniently see together and the focusing has to be redone for each one. Moreover, the place on the object being observed is generally not localizable on the object.

As a general rule, the objective lens of a fluorescence microscope magnifies from 10 to 40 times, while the eyepiece enlarges from 10 to 40 times. If the luminance of the object being observed is on the order of $10^6$ cd/m$^2$, the brightness is only a few lux at the output of the eyepiece.

When, as is the case in immunofluorescence, it is desired to employ such a technique in order to examine reactions, there is required special preparation, which is the result of thorough work. In the case of immunofluorescence, first a blood sample is taken or a biopsy is carried out on a patient. When, for example, it is a matter of seeking antibodies in the serum of such patient, an antiglobulin serum which is marked, for example, with ITCF, and test antigens, which are prepared in advance are used. The antiglobulin serum is titrated, that is, its dilution is known, and what is used is either the maximum dilution which should give the maximum fluorescence or the dilution just below that if the serum has a high titer. With respect to the serum of the patient, successive dilutions are also prepared, which enable an approximate form of quantification of the intensity of the antibody-antigen reaction and of its evolution in time to be obtained: in effect, if antibodies for high dilutions are still found, it can be deduced that there were many antibodies in the serum of the patient; if, a few weeks after observation, the reaction is positive for a higher dilution, it can be deduced that the disease is evolving, etc.

It will be noted that only experience can indicate, in advance, which are the interesting dilutions to use for which disease. The dilutions used for the same disease can therefore vary from one laboratory to another and even from one laboratory technician to another. It is therefore only possible to know if a patient is ill or not and if his disease is developing in the sense of worsening or of a cure. It is therefore interesting to be able to improve upon the known system for using the technique of immunofluorescence to obtain a true quantification of the antibodies.

Moreover, as mentioned above, the preparation is placed on a slide or the cells of a plate, which will be placed on the stage of the microscope and moved under the lens so as to enable the successive examination of the plurality of cells. In addition to the fact that this is tiresome work requiring patience, especially when successive dilutions must be studied, the passage of a reaction to negativity must be determined, and images with low luminosity and with only slightly distinct color must be looked at, it will be noted that the results can only be subjective and even aleatory since they depend on the perception by the eye.

In effect, it is the visual sense of the laboratory technician which makes him decide on the criteria of color and luminous intensity, and on the positivity or negativity of a reaction. In view of the fact that sera of very variable titers and with sometimes very high dilutions are used, the image to be studied, when a reaction is weakly positive or negative, can be very slightly luminous, which causes various problems.

The colors to clearly distinguish in immunofluorescence are most often ITCF green, Evans Blue red and rhodamine red, at illuminations varying from approximately 1 to $10^{-4}$ lux.

The first visual factor entering into immunofluorescence is the so-called Purkinje phenomenon, which notes that the curve of sensitivity of the eye in daylight vision (more than 10 cd/m$^2$) shows a maximum in the green and that this maximum shifts towards the blue progressively as the ambient luminance is lowered.

Moreover, the eye is overall progressively less sensitive to all wavelengths as darkness approaches. Thus, two radiations, for example one green and the other red, which would be perceived subjectively as having equivalent intensity in daylight would give the impression that the green is much more intense than the red in darkness. The eye cannot validly compare two colors unless the luminance does not change. If the luminance increases, the green seems to become more yellow and the red more orange. Consequently, in the observation of immunofluorescence, there is no risk that the green fluorescence will not be seen; however, a loss of definition takes place in low lighting, and there is poor visibility of the red. In the case of a mixture of green fluorescence and red fluorescence, the eye can see only the green, or sees the green more yellow than it is, if there is more green than red. If there is as much green as red, it may see yellow where there is none.

Moreover, the eye is subject to errors in vision due to inhibitions which its cells exert on each other. For example, the contrast between two contiguous fields of vision, one clear, the other dark, is exaggerated, the boundary being edged with a darker black and a lighter white. The eye thus reinforces the boundaries. Likewise, if one stares at an object which is, for example, red edged with green, and then at a white or gray background, then an illusive image, which is green edged with red, will be seen to appear on the background. Moreover the perception of black varies with the luminance.

With respect to visual acuity, it is known that such does not decrease in an equal manner for all wavelengths: thus, below 1 to 2 lux, it is less good for red than for green, but at $10^{-4}$ lux it is bad both for red and green. The eye cannot then separate better than 2 to 3 $\mu$m, with a microscope enlarging 400 times and which theoretically enables separation of two points distant by 0.25 $\mu$m apart for an eye with visual acuity of ten tenths.

Additionally, the eye is dependent on time when the luminance is low. The cones of the eye take from 7 to 10 minutes to reach their best yield when the luminance is between 1 and 0.1 cd/m$^2$. For lower luminance, the cones stop adapting themselves and the rods of the eye take over, with a much better sensitivity, but with very bad acuity. Consequently, not only must time be taken during examinations to allow the eye time to adapt, but also vision is then particularly defective.

Finally, the eye is subject to tiredness which modifies its possibilities.

Thus, the present use of the immunofluorescence technique has numerous imperfections which do not provide a true quantification. However, the interest in this technique is considerable, since it enables diagnosis, discovery and the study of human and animal diseases as well as the progress of biological and pathological research.

Among other examples, immunofluorescence provides rapid showing of numerous germs and parasites, such as those of anthrax, of certain meningitis, of whooping cough and of brucellosis, of several mycoses, of diphtheria, of certain pneumonias, of colon bacillus, of salmonellosis and of shigellosis, of toxoplasmosis, of histoplasmosis, of mononucleosis, of pasteurellosis, of leptospirosis, of listeriosis, of trichinosis, of tuberculosis, of syphillis, of streptococcal, staphylococcal, pyocyanical and gonococcal infestations, of paludism, of distomatosis, of bilharziosis, etc. Moreover, it enables detection of antinuclear antibodies, antiskins, viruses such as the herpes virus, etc., as well as the operation of HLA tests.

Thus, the principal object of the present invention is to produce a system overcoming the disadvantages of the known system described above and providing advantageous use of all the possibilities of the immunofluorescence method by increasing the quality of the results obtained and by simplifying the operation. This principal object is attained in particular by freeing the use of the human eye and by automating the system, so as to enable true quantification of the immunofluoroescence reactions.

For this purpose, in accordance with the invention, there is provided a system for the automatic observation and quantification of phenomena capable of being detected by fluorescence and appearing within a localized zone, said system comprising a source of radiation, possibly with an excitation filter in order to send onto said localized zone excitation radiation capable of producing the fluorescence, optical observation means for the localized zone, and at least one filter intended to block the excitation radiation and arranged in the path of the luminous fluorescence radiation emanating from said localized zone. The system is remarkable in that it comprises a picture-taking tube (pickup or camera tube) with variable gain successively examining the localized zone through the optical observation means and through at least two differently colored filters selected in accordance with the wavelength of the luminous fluorescence radiation, memory means for recording the electric signals corresponding to the individual colored images seen by the picture-taking tube, means for simultaneously recovering the electric signals at the output of the memories and means for varying the gain of the picture-taking tube such that the amplitude of its output signals is always greater than a threshold beneath which the remanence of the tube becomes a problem.

Thus, due to the invention, two important difficulties are overcome in the observation and quantification of fluorescent phenomena, that is low yield and transience, at the same time taking advantage of the fact that the fluorescent phenomena observed are immobile and that it is therefore possible to transmit separately and successively, then to superpose the differently colored fixed images of the same phenomenon so as to analyze and reconstitute the fluorescent phenomenon. In the case of immunofluorescence, it is generally sufficient to use only two different colored images, that is a red image and a green image; however, in certain cases, it may be preferable to use a third image, for example blue.

It will be noted that the system in accordance with the invention is able to dispense with use of the human eye which, as mentioned above, is incapable of carrying out real quantification. Moreover, this system requires only a single picture-taking tube, such that perfect superposition of individual colored images, point to point, can be obtained, and the disadvantages of color television devices with several tubes, which are due to the dispersion of the characteristics of same, are avoided.

Preferably, in the system in accordance with the invention, the picture-taking tube is used, moreover, to examine the localized zone directly in order to give thereto a black and white image which is used for the focusing, either manual or automatic, of the picture-taking tube. Thus, such a black and white image, which may have high definition, enables the focusing of the optical observation means, such that the luminous beam of fluorescence is exactly focused on the photocathode of the picture-taking tube during the observation of individual colored images.

Moreover, so as to further minimize the effects of the remanence of the tube, it is beneficial for the picture-taking tube to be either masked or blocked between two successive examinations through successive colored filters and/or between one examination through a colored filter and the direct examination intended to give the black and white representation.

For this purpose, it is practical to provide a disc which contains at least one window or peripheral indentation corresponding to the direct examination in black and white, colored filters and opaque areas, and which is rotated so as to successively bring the window, filters and opaque areas to intercept the luminous beam of fluorescence sent to the picture-taking tube.

Such a disc is driven by a motor whose operation is, of course, synchronized with the rest of the system in accordance with the invention and, in particular, with the placing in memory of the signals corresponding to the individual colored images. In order to ensure at least in part such synchronization, it is preferable to provide fixed sensors, for example optoelectronic sensors, cooperating with reference marks of the disc, for example windows.

In spite of the presence of the blocking filter(s) on the luminous beam of fluorescence, part of the excitation radiation reaches the picture-taking tube. Thus, in order to overcome this disadvantage and in order to take into account the fact that this part of the excitation radiation intervenes differently for the various colored images, individual adjustments for the level of the background are provided for each colored image and these adjustments are under the control of the gain of the picture tube, such that these adjustments are correct for all gain values of this tube.

Moreover, it is well known that the image of a luminous area generally has more intense illumination at its center than at its edges, the importance of this phenomenon increasing as the luminous intensity increases and vice-versa. The result is that the background of the images observed has a dome shape which does not correspond to a variation in real illumination of the luminous area itself. Thus, in order to overcome this disadvantage, in accordance with the invention there is provided a generator which is under the control of the amplification of the picture tube and produces dished signals intended to cancel the dome background of the signals coming from the picture tube.

Of course, this natural dome effect is spatial and not linear, such that it is advantageous to provide a correction by dished signals, both in the direction of the lines of the image and in the direction of the frame.

Moreover, it is preferable to provide, downstream of the memory means, background suppression means which can provide integration and rectification of the image signals and the subtraction of the signals thus obtained from real signals.

In order further to increase the purity of the colored signals obtained, it is preferable to provide means for producing, on the one hand, the difference between the signals coming from the first colored filter and those coming from the second colored filter and, on the other hand, the difference between the signals coming from the second colored filter and those coming from the first colored filter. Thus, each of the differences corresponds strictly to one of the colors from which has been totally removed the part of the other color which should have been removed by the filters, but which has not been so removed due to the imperfection of the filters.

These differences of signals can therefore serve as data for the quantification of the phenomena observed.

Finally, in order to remove any influence due to artifacts, means are provided which are intended to remove such. Such means can include delay means, clipping means, amplification means and means for addition and/or subtraction enabling each artifact to be removed by means of a portion of itself.

The attached drawings will enable an understanding of how the invention may be produced.

FIG. 4 and FIGS. 5a, 5b and 5c illustrate the dome correction of the video signals of the picture tube.

Figure 1:
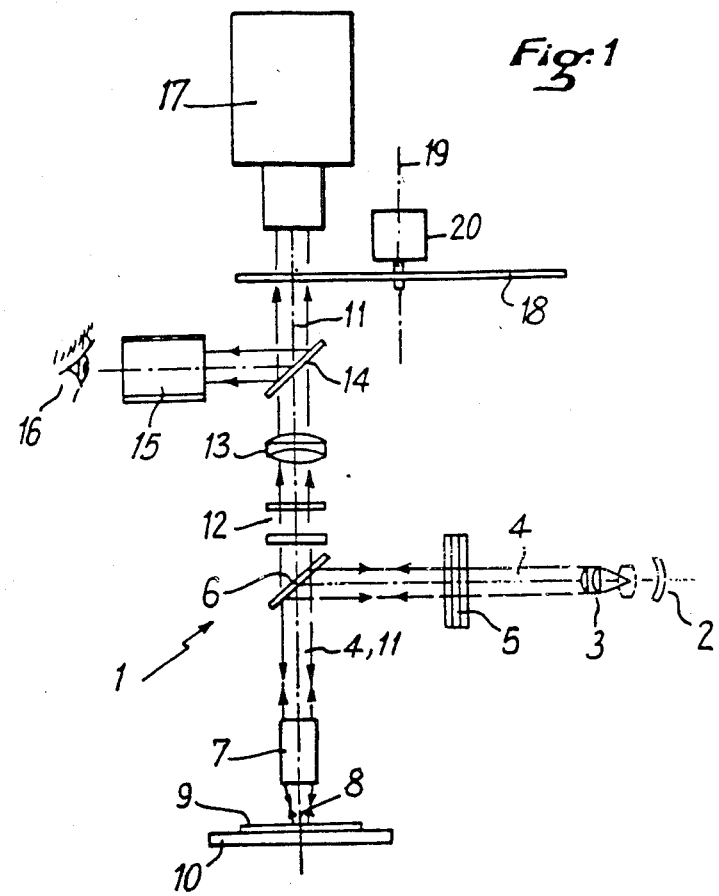
FIG. 1 illustrates schematically an embodiment of the picture-taking assembly of the system in accordance with the invention.

The picture-taking assembly 1 in accordance with the invention, shown by FIG. 1, comprises a luminous source 2 of high luminance which, together with a condenser 3, emits a beam 4 of parallel rays, traversing excitation filters 5. The beam 4 thus filtered strikes a dichroic mirror 6 which deflects it 90° and transmits it to objective lens 7 which concentrates the beam on a localized zone 8 in which a fluorescent phenomenon appears. This localized zone can be a part of a slide or a cell of a plate, the slide or plate 9 being carried by a stage 10. Where plate 9 contains in zone 8 a plurality of cells to be examined, a mechanism for relative movement of the stage 10 in relation to the lens 7 is provided (see FIGS. 9 to 11), such that each of the cells passes in turn under said objective 7 (see mechanism 37 of FIG. 3).

The emission of fluorescence produced by the phenomenon of the localized zone 8 is formed by lens 7 into a parallel beam 11, transmitted with the reflected part of beam 4, to the dichroic mirror 6 which deflects the reflected part of beam 4 back towards source 2. The fluorescence beam 11 then passes through the blocking filters 12 and lens 13. Optionally, a second dichroic mirror 14 deflects a part of beam 11 toward an eyepiece 15 behind which the eye 16 of an observer may be placed.

Beam 11 forms an image of zone 8 on the photocathode of a picture tube 17, a disc 18 rotating around its axis 19 under the action of a motor 20, being interposed in the path of beam 11 transmitted to the picture tube 17.

It will be noted that the assembly of elements 2 to 15 constitutes a microscope of the type used until now in the art of immunofluorescence and that the present invention is concerned only with the combination of elements 17 to 20. Moreover, for the operation of the invention, the dichroic mirror 14 and the eyepiece 15 are not indispensable and could be removed.

Figure 2:
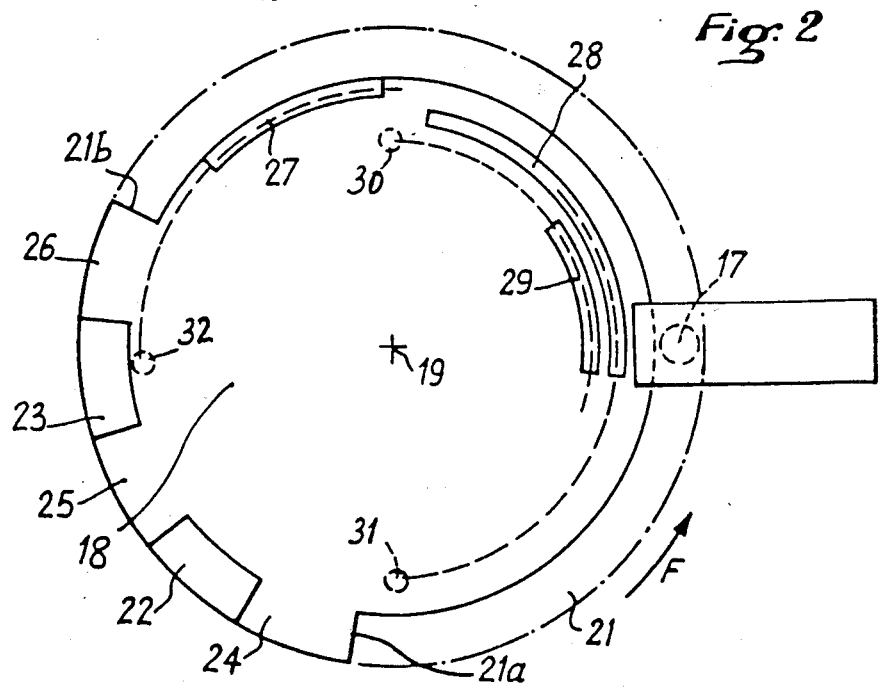
FIG. 2 is a planar view of the embodiment of the disc used in the assembly of FIG. 1.

It will also be noted that the structure of the assembly 1 of FIG. 1 is such that zone 8 is illuminated by the reflected part of beam 4. Of course, this arrangement is not limiting and zone 8 could, for example, be examined by transparency rather than by reflection, elements 12, 13 and 17 to 20 then being located on the opposite side of lens 7 in relation to stage 10.

Where the assembly 1 of FIG. 1 is intended for the examination of immunofluorescence by means of ITCF, source 2 can be of the types commercially known under the names HBO 50, HBO 100 or HBO 200, which are capable of providing on zone 8 illumination on the order of 50,000 to 100,000 lux, such that, since the reemissions of fluorescence have a yield on the order of 1/100 to 1/1000, beam 11 may have an illumination of a few hundred lux. In addition, the excitation filters 5 may be selected from among those known commercially under the names BG12, LP 480 or KP490; they are thus intended to provide a maximum of excitation in the blue (between 450 and 500 nm) and to very strongly attenuate the radiation above 500 nm. The dichroic mirror 6 is provided in this application in order to allow the yellow wavelengths of beam 11 to pass in the direction of the picture-taking tube 17, but to send back towards source 2 the blue radiation of the reflected beam 4. The action of the dichroic mirror 6 is reinforced by the blocking filters 12 (for example of the type commercially known by the name LP520) which block the blue and allow only radiation of a wavelength greater than 500 nm to pass, thus acting as a high-pass filter. The lens 13, for example of the OPTOVAR type, has as its object the movement of the image focus of objective lens 7 in order to give a more uniform illumination of the object being examined. As is shown in FIG. 2, the disc 18, composed of a black colored material which is opaque to the radiation of beam 11, contains a large peripheral indentation (or cut out part) 21, as well as two peripheral red and green filters 22 and 23. Indentation 21 and filters 22 and 23 are arranged on disc 18 so as to be able to be brought successively straight below the picture tube 17 when the disc turns (arrow F) under the action of motor 20; end 21a of indentation 21 is separated from filter 22 by an opaque part 24 of disc 18; likewise, filters 22 and 23 are separated from each other by an opaque part 25 of disc 18, while another opaque part 26 of disc 18 is arranged between the beginning of indentation 21 and filter 23. The object of opaque parts 24, 25 and 26 is to mask tube 17 between two measurements so as to discharge it and in part avoid the effect of its own remanence. An anti-remanence effect could also be obtained by blocking the operation of the tube between two measurements.

Finally windows or reflecting zones (which more generally will be called "tracks") 27, 28 and 29 are made in disc 18, so as to be able to cooperate during the rotation of said disc with fixed opto-electronic devices 30, 31 and 32 (see also FIG. 3) for purposes of synchronization, as will be described below.

Thus, when disc 18 turns, several sequences occur in succession:

1. While indentation 21 is located perpendicular to the picture tube 17, it can observe the fluorescent zone 8 under the best conditions of definition, sensitivity and quantity of light. It can then produce a black and white image of this fluorescent zone on a television screen 33 (see FIG. 3). The connection between the picture tube 17 and the television screen 33 is produced by a video cable 34, that is without limitation of a passing band, before interposition of a device $35_{NB}$ for pre-processing of the black and white video signals. During this sequence of observation in black and white of zone 8, the signal produced by tube 17 is large (or at least larger than those produced during other sequences), so it is preferable to focus the image during this sequence, either manually or automatically. Manual focusing is carried out by the operator by observing the black and white image on screen 33. For automatic focusing, a device 36 for automatic focusing of any known type is provided, said device receiving the black and white video signals coming from the pre-processing device $35_{NB}$ and consequently controlling the mechanism 37 for relative movement of the stage 10 in relation to the lens 7. In addition, mechanism 37 receives orders from the opto-electronic device 30 for the other relative stage-lens movements and for the control of motor 20 of disc 18.

The detailed description of an embodiment of the automatic mechanisms necessary for the control of the relative movements will be found below.

2. When opaque part 24 comes opposite picture tube 17, the tube no longer receives beam 11, but a level of black which enables it to discharge itself and to counteract the effect of remanence of tube 17.

3. While the red filter 22 is opposite tube 17, tube 17 receives a red image or frame of zone 8.

4. The red frame is followed by reception of a new level of black due to the opaque part 25 following red filter 22.

5. Then, green filter 23 follows opaque part 25 under the picture tube 17, such that the tube receives a green image or frame of zone 8.

6. Finally, green filter 23 is followed under tube 17 by opaque part 26 which provides it with a new level of black. After part 26, indentation 21 again comes straight below the picture tube 17, for a new cycle.

During the observations of zone 8 by the red filter 22 (point 3 above), the video signals emanating from tube 17, after pre-processing in a device $35_R$, are stored in a red memory $38_R$. Likewise, during the observations of zone 8 by the green filter 23 (point 5 above), the video signals emanating from tube 17, after pre-processing in a device $35_V$, are stored in a green memory $38_V$. Preferably, memories $38_R$ and $38_V$ are of the so-called "refreshed memory" type.

Thus, on each turn of disc 18, it is possible to transform the successive green and red video signals into simultaneous signals. In effect, it is sufficient to read the two memories $38_R$ and $38_V$ simultaneously such that each point of one of the green or red images stored is superposed on the corresponding point of the other image. The simultaneous reading of the two memories $38_R$ and $38_V$ therefore enables superposition of the green and red images to be obtained. The storing of the green and red signals in the memories $38_R$ and $38_V$ is synchronized with the rotation of disc 18, due to the opto-electronic device 31. The outputs of memories $38_R$ and $38_V$ can be connected to a color television 39 on the screen of which the colored image of the corresponding zone 8 appears. Similarly, these outputs can be connected to a video recorder 40 for recording the colored images.

The system in accordance with the invention thus allows the use of only one picture tube for both the green and the red, such that all the problems of superposition and dispersion of characteristics curves, which are normally found in television cameras using a specific tube for each color, are eliminated.

Figure 3:
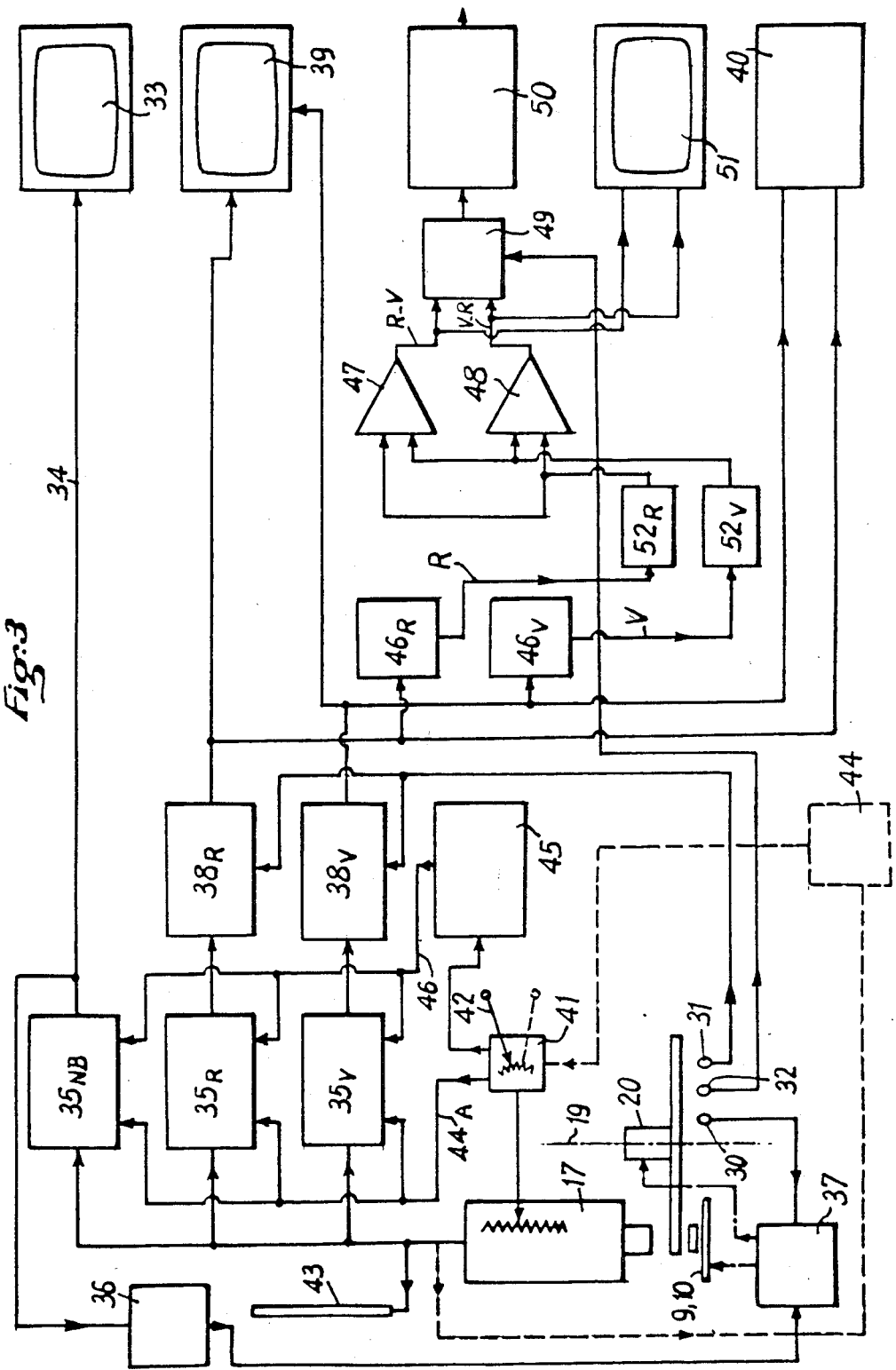
FIG. 3 is a simplified schematic block diagram of the electronic assembly of the system in accordance with the invention.

Although in the example of FIG. 3 only two colors (red and green) were used to analyze the fluorescence of zone 8, it goes without saying that a third color filter, blue for example, could be provided on disc 18, the filter being associated with a third memory. It would thus be possible to analyze all the visible spectrum, which could be useful in certain cases of excitation in ultra-violet.

Picture tube 17 must have very high sensitivity and, in addition, this sensitivity must be able to be varied within a wide range. Thus, it is preferable that this picture tube be of the type comprising an incorporated electron multiplier in addition to the usual image analyzer of the VIDICON tubes. In that manner, the tube may have high gain, on the order of 1,500 to 2,500, but which is variable dependent upon the acceleration voltage of the electron multiplier. By way of example, tubes known commercially by the names of NOCTICON 9655, NOCTICON 9559 and SUPER NOCTICON have been used satisfactorily. In such tubes, the acceleration voltage of the electron multiplier can vary from 3000 to 9000 volts for example, causing a variation of sensitivity in a ratio of 1 to 400. They enable analysis of images which have an illumination of $10^{-5}$ lux and which are formed on their photocathode having a 25 mm diameter.

As will be seen below, the sensitivity of the picture tube 17 is thus adjusted or controlled with precision and the control of this sensitivity also controls different corrections necessary to obtain good quantification.

However, picture or pickup tubes with high variable sensitivity of the type mentioned above have the disadvantage of having high remanence, such that the weak signals are amplified to an exaggerated extent whereas strong signals are only slightly affected.

The most marked effect of this remanence is that, during the analysis of a frame, the preceding frame is not yet erased. Experience has shown that this effect is only bothersome if the intensity of the signal at the output of tube 17 is lower than a lower threshold, for example equal to 25 nA. Now, the maximum intensity of the signal at the output of tube 17 is several times greater (on the order for example of 500 nA) than this lower threshold, such that it is possible to adjust the acceleration voltage of the electron multiplier of tube 17 in order never to go below the threshold. As is shown on FIG. 3, the system in accordance with the invention contains a device 41 for adjusting the (Extra High Voltage) of the picture tube 17, that is the amplification gain of the tube. The control of device 41 may be manual, through the activation of a component 42, with the operator adjusting the position of component 42 dependent upon indications of the amplitude of the output video signals of tube 17, which indications are provided by a view-meter 43. Optionally, the adjustment can be automatic by means of a device 44 receiving the output signals from the picture tube 17. Thus, manually or automatically, the acceleration voltage of the electron multiplier may be controlled to increase the intensity of the output signal current as soon as the intensity nears, while decreasing, the lower threshold.

Moreover, experience has shown that in spite of the dichroic mirror 6 and filters 12, a certain quantity of light emanating from the excitation source 2 reaches tube 17, and constitutes a background whose illumination can be of a few hundredths or thousandths of lux. Thus, for weak signal levels, the useful signal could be lower than the value of the background. It is therefore necessary to eliminate this phenomenon which would render quantification practically impossible. However, it must be taken into account that the attenuations of the filters are different depending on the wavelengths (see FIGS. 4 and 5), and the background does not have the same value for red frames as for green frames. Thus, it is necessary to provide separate adjustments for black and white, for red and for green. These separate adjustments are for example provided in devices $35_{NB}$, $35_R$ and $35_V$ for pre-processing of the video signals, which, for the most part, are amplifiers. Due to these adjustments, the two green and red signals can be rendered equal on a corresponding zero level for the red and green backgrounds. However, such separate adjustments are only valid for a determined level of amplification or gain of the electron multiplier of tube 17. Now, as has been seen above, it is indispensable to vary the level of amplification of the electron multiplier. Thus, it is absolutely necessary to correlate the magnitude of the corrections made to the black and white, red and green backgrounds with the gain of tube 17. It can be noted in FIG. 3 that the device 41 for control of the high voltage of the electron multiplier element of tube 17 also controls the magnitude of the correction of the level of the black and white, red and green backgrounds by means of a line 44A which brings the individual gains of devices $35_{NB}$, $35_R$ and $35_V$ under the control of picture-taking tube 44.

In addition, normally, it is known that the brightness of a luminous area defined by the edges is more intense at the center than in the region of the edges, such that, transversely to the area, the brightness of same has the form of a dome.

FIGS. 4 and 5 illustrate these phenomena. FIG. 4 shows the attenuation curve (A) of the brightness E (in lux) of a zone 8 as a function of the wavelength λ (in nm) of the light received from the zone. It can be noted that this attenuation is greater for red than for green. Moreover, if, as in FIG. 5a, the brightness E along the width L of zone 8 is shown, it can be seen that the background of the zone has the shape of a dome D, from which peaks P of the fluorescent phenomena appear.

In order to counteract this dome effect, the system in accordance with the invention contains a generator 45 emitting AD signals of a dish shape which is the inverse of the domes. Generator 45 is connected to the device 41 for control of the gain of tube 17, such that the AD signals are of a shape corresponding to the gain. By means of a line 46 the AD signals are transmitted to the various pre-processing devices $35_{NB}$, $35_R$ and $35_V$, in which they are added to the D+P signals received from tube 17. The result is that the dome effect (see FIG. 5b) disappears. Moreover, due to the action of device 41, by means of line 44A, it is possible to bring, as indicated above, the green and red signals to the same level (FIG. 5c).

Of course, since the dome phenomenon is spatial and not linear, device 45 brings about a correction not only in the direction of the lines, but also in the direction of the frames.

By means of automatic background correction devices $46_R$ and $46_V$, and possibly of anti-artifact devices $52_R$ and $52_V$ (see FIG. 3), the red and green signals read into memories $38_R$ and $38_V$ are sent to two subtractors 47 and 48, delivering at their outputs R-V and V-R signals, respectively, which are transmitted to a calculator 49, controlled by the opto-electronic device 32, then to a display device 50 for visualizing the results and from there to a computer (not shown). Optionally, these R-V and V-R signals produce a colored image on a color television screen 51.

Figure 6:
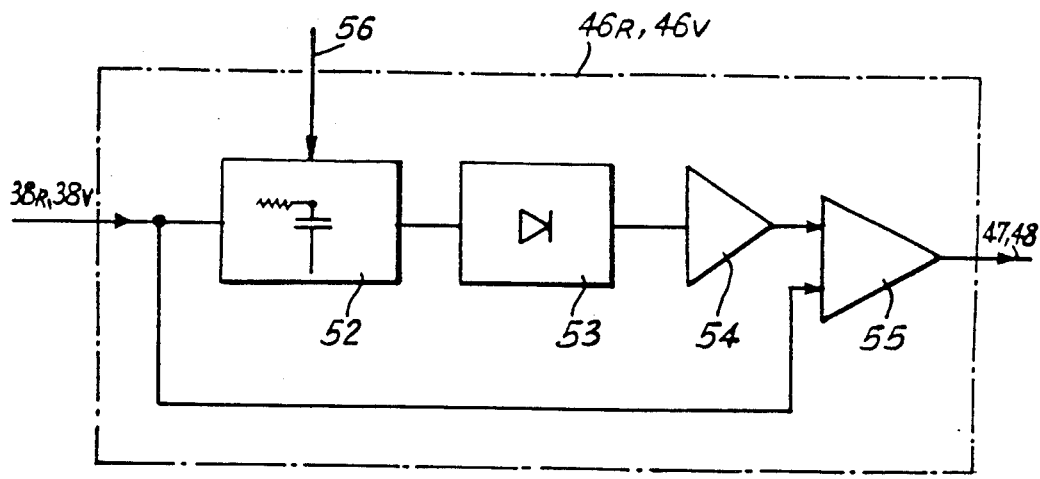
FIG. 6 is a schematic block diagram of a device for background correction of the colored signals.

As is shown in FIG. 6, each of the automatic background correction devices $46_R$ and $46_V$ contains an integrator 52, a rectifier 53, possibly an amplifier 54 and a subtractor 55 receiving on the one hand the signal from the chain 52, 53, 54 and on the other hand, directly, the signal from memories $38_R$ or $38_V$.

The structure of devices $46_R$ and $46_V$ is due to the observation that the fluorescent phenomena observed (peaks P of FIG. 5) are small in relation to the total surface of zone 8 observed: for example, they only represent a few $\mu m^2$ of this total area which is on the order of a few $mm^2$. Thus, the integration of the total signal as carried out by integrators 52 makes the useful signal P disappear in order to produce only the background. However, in order to avoid cumulative integration, it is absolutely necessary to block the operation of integrators 52 between frames, and this is carried out by means of a control 56. The signal integrated by the integrators 52 is then rectified by rectifiers 53 which give a continuous uniform voltage which, optionally amplified by the amplifiers 54, is subtracted in subtractors 55 from the red or green signals.

Theoretically, at the output of devices $46_R$ and $46_V$, the signals should be either red or green. However, due to the imperfection of the filters used, there remains some green in the red signal and some red in the green signal. Thus, in order to avoid this disadvantage the subtractions R-V and V-R are carried out by means of subtractors 47 and 48 downstream of devices $46_R$ and $46_V$. In this manner, at the output of the subtractors, the R-V signal represents the red contained in zone 8, whereas the V-R signal represents the green contained in zone 8. The colored image on screen 51 is therefore a theoretical image of zone 8.

In addition, the signals emanating from memories $38_R$ and $38_V$ can contain artifacts, that is, parasite signals, which do not correspond to the reality of the object which it is wished to observe. For example, in the case of immunofluorescence, the artifacts are all the objects visible on the preparation, but foreign to the reaction being studied: they may be composed of greasy traces on a poorly cleaned slide, poorly filtered stopper particles, etc., and they produce signals which are often much more luminous and which have a much larger surface than the elements of the reaction in question.

Figure 8:
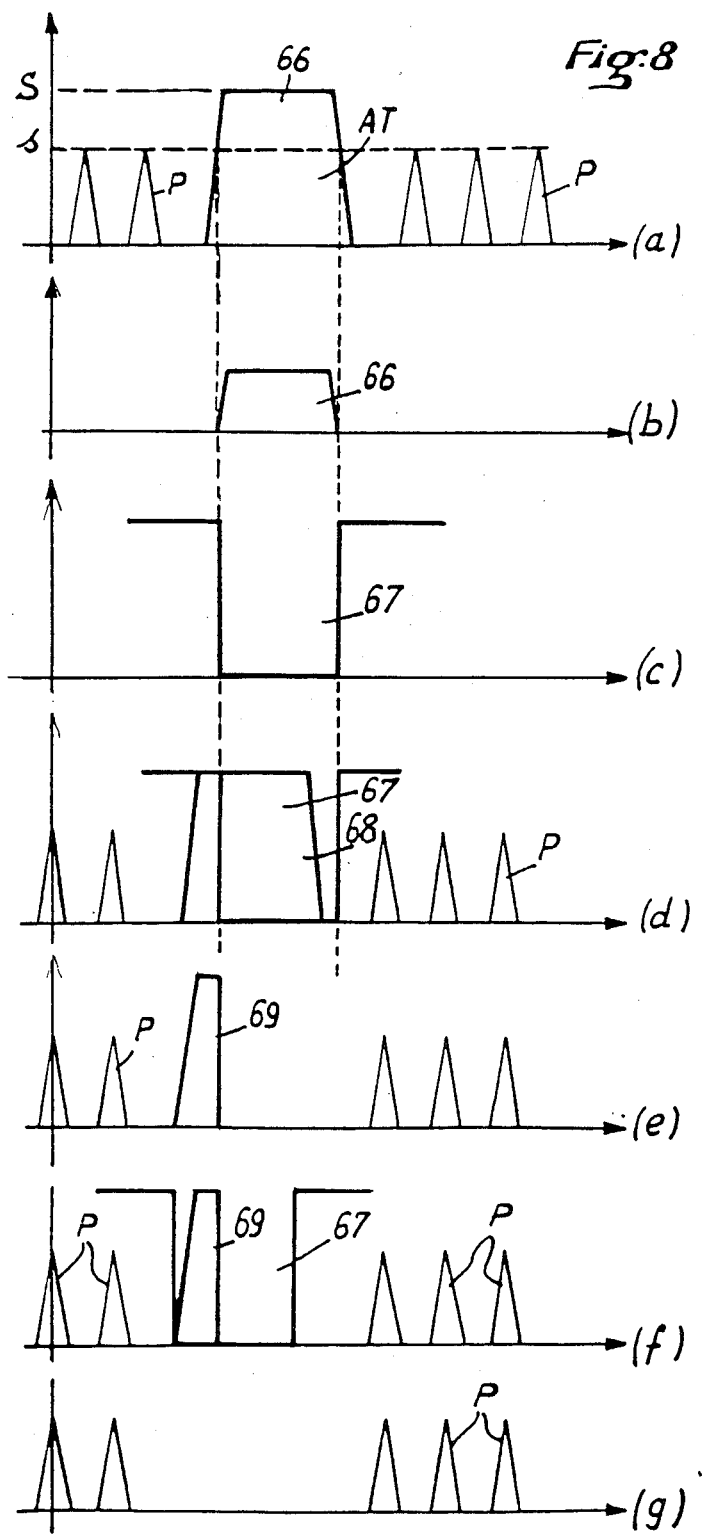

In FIG. 8a, an artifact AT intervening in the middle of useful signals P is shown. It will be noticed that due to the limited storage capacity of memories $38_R$ and $38_V$, such an artifact AT has already been clipped at a level S.

In order to be able to remove the remaining, unclipped part of the artifacts AT, the system in accordance with the invention contains two devices $52_R$ and $52_V$ which receive the signals emanating respectively from memories $38_R$ and $38_V$ and send corrected signals to subtractors 47 and 48 respectively.

Figure 7:
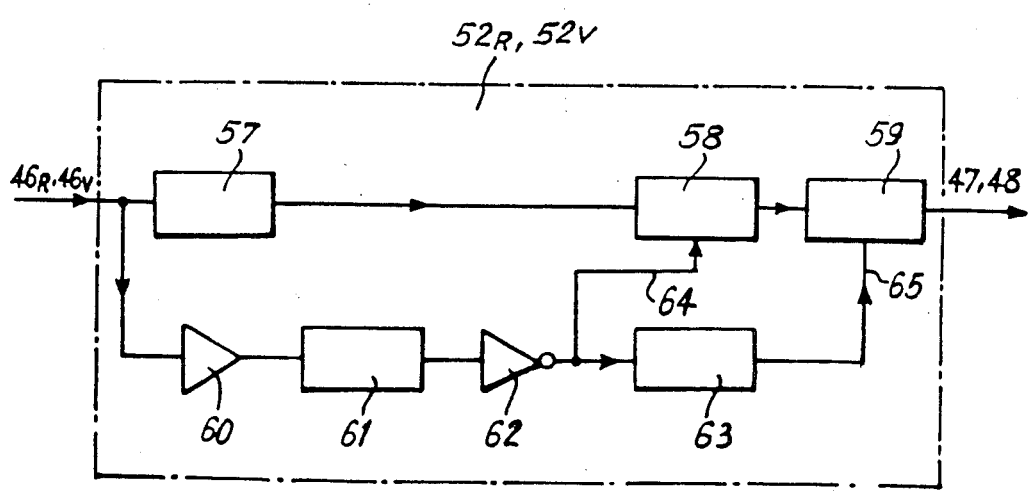
FIG. 7 and FIGS. 8a to 8g illustrate the cancellation of the artifacts from the video signals.

As is shown in FIG. 7, each of the anti-artifact devices $52_R$ or $52_V$ contains two parallel channels, that is one channel containing, from the input to the output, a delay line 57 and two adders 58 and 59, and one channel containing, also from the input to the output, an optional amplifier 60, a clipper 61, an inverting amplifier 62 and a delay line 63. Connections 64 and 65 are provided respectively between the output of the inverting amplifier 62 and the adder 58, and between the output of the delay line and the adder 59. The operation of devices $52_R$ and $52_V$ is described with regard to FIGS. 8b to 8g.

The clipper 61 removes, in artifact AT, the part 66 between the level s of useful signals P and the maximum level S (imposed by memories $38_R$ and $38_V$) in order to create an isolated signal therefrom (see FIG. 8b). This part 66 of signal AT is amplified and inverted by the inverting amplifier 62 in order to become an inverted rectangular signal 67 (see FIG. 8c).

In adder 58, the inverted rectangular signal 67 is added to the signal AT+P, delayed by the delay line 57, such that the front part 68 of the AT signal is removed by said rectangular signal (see FIGS. 8d and 8e). Then, only the back part 69 of the AT signal remains (FIG. 8e).

However, in adder 59 the signal of FIG. 8e is added to the inverted rectangular signal 67, delayed by delay line 63, such that the back part 69 is removed (FIG. 8f).

At the output of devices $52_R$ and $52_V$ there therefore remains only the useful part of the AT+P signal, that is the peaks P (FIG. 8g).

With regard to the recording of the colored images, it will be noticed that the video recorder 40 can be of any conventional type capable of recording different colored signals. However, it is possible to use a simple black and white video recorder by allocating alternatively even (or odd) frames to one of the colors (red or green) and the odd (or even) frames to the other of said colors (green or red).

Figure 9:
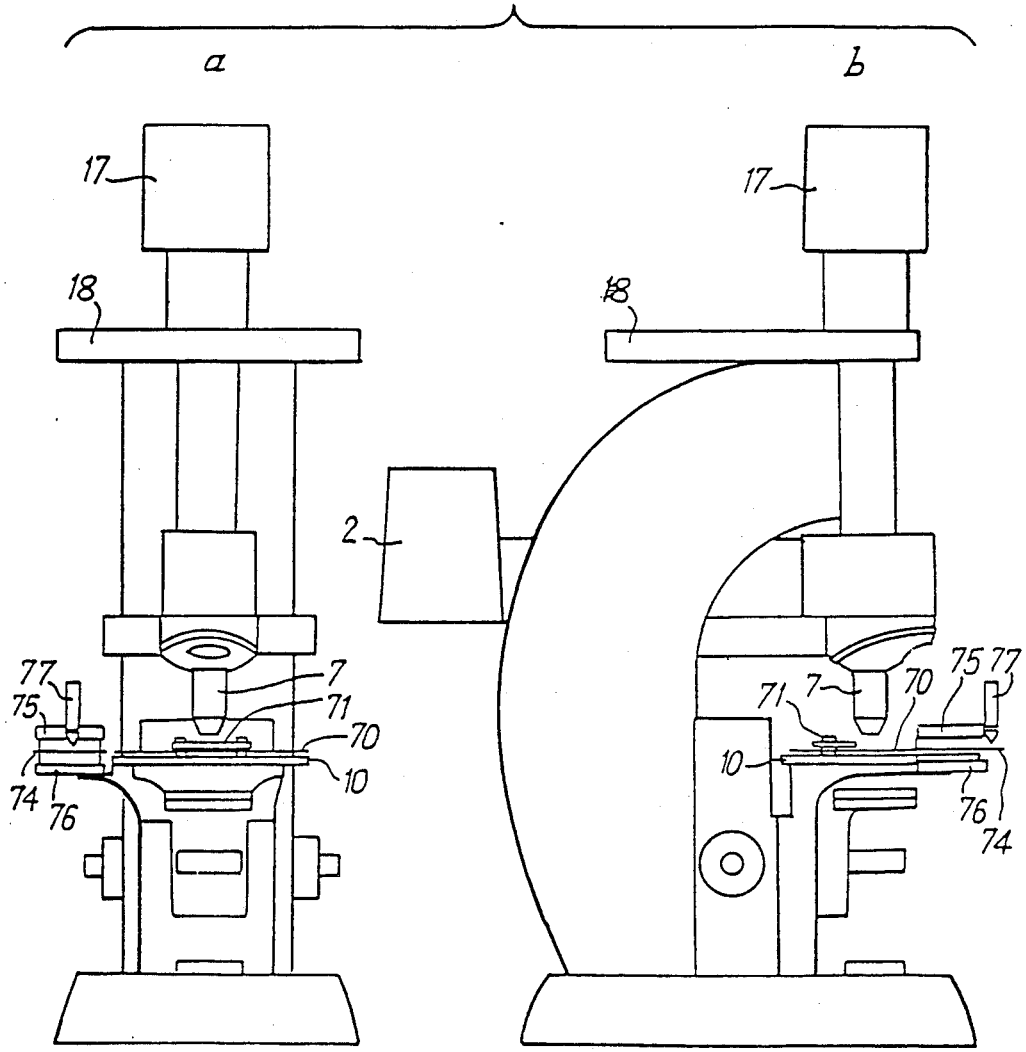
FIGS. 9a and 9b illustrate a overview of an embodiment of the devices for controlling the movement of the stage in relation to the objective lens, from the front and side, respectively.
Figure 10:
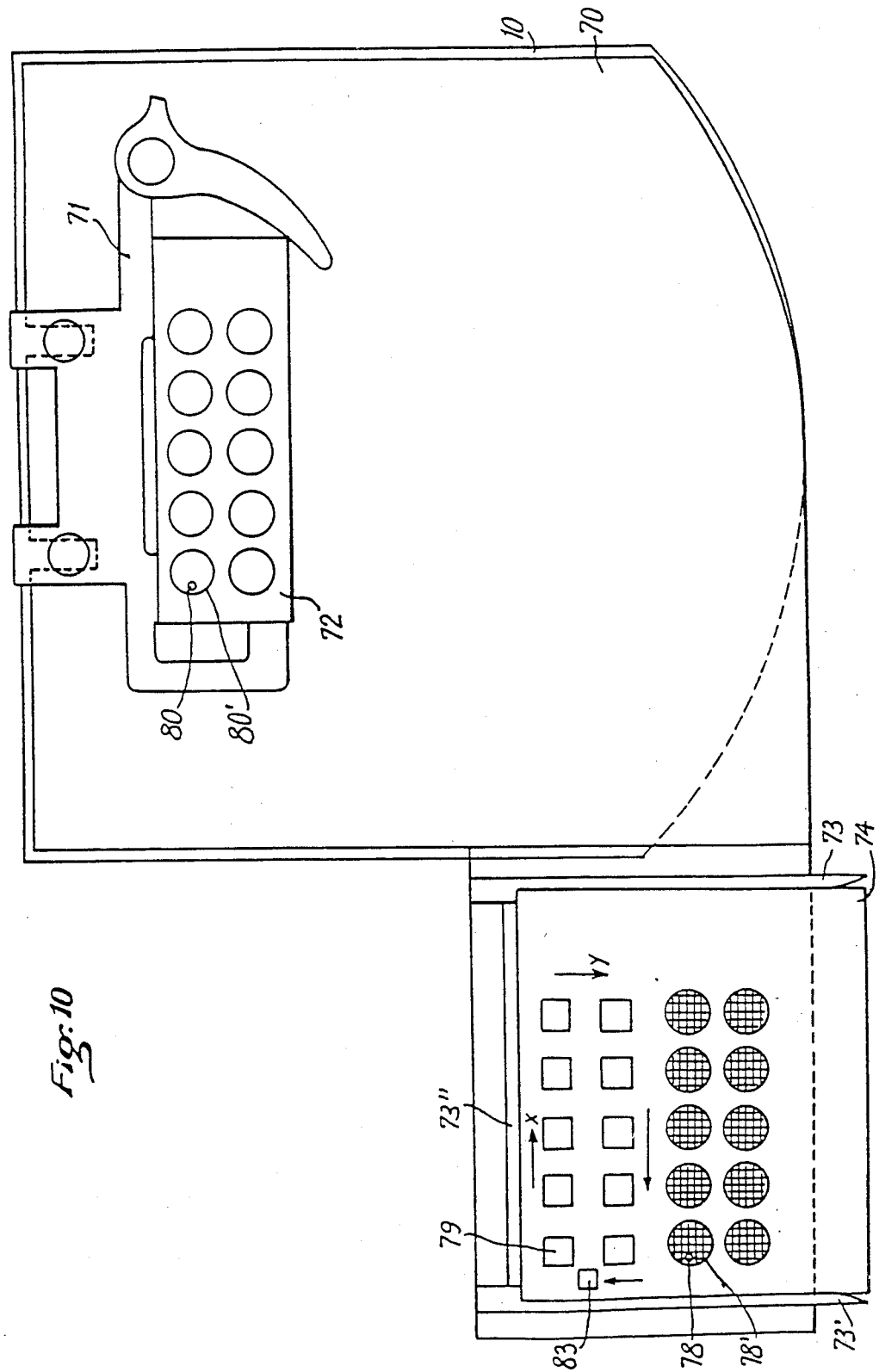
FIG. 10 is a detailed planar view of an embodiment of the automatic guidance of the movements of the stage.
Figure 11:
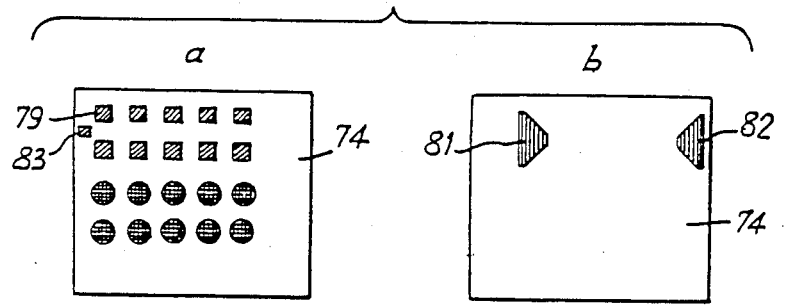
FIGS. 11a and 11b illustrate an embodiment of the auxiliary plates of the automatic system, viewed from above and below, respectively.

It has been stated above that optoelectronic signals control movements of the stage 10 in relation to the lens, and in particular in the X and Y directions. A simple method for producing the necessary automatic mechanisms is shown in FIGS. 9a, 9b and 10, where it can be seen that a thin complementary stage 70, tightened to the slide-bearing device 71, in which the slide 72 to be examined is immobilized, has been arranged. This complementary stage contains, to the left of the operator in FIG. 10 (but to the right, if so desired), guides 73 and 73′ in which may be inserted auxiliary movable plates 74 (such as those shown in FIGS. 10, 11a and 11b) whose forward movement is limited by a stopping abutment 73″. This complementary stage 70 is itself inserted between two casings, 75 for the upper part and 76 for the lower part (shown in FIG. 9), enclosing an optoelectronic device composed of assemblies of photodiodes and "LED" diodes operating either by reflection or by transparency. In the front of the upper part 75 a small diameter cylinder 77 is fixed which, for example, has in its interior an LED diode at the top and a lens at the lower end, such that a luminous point 78 appears on the image well 78′ of the auxiliary movable plate 74. It can be seen in FIG. 10 that the auxiliary movable plate 74 in particular contains, on the one hand the visible image 78′ of the wells, such as is presented by the real wells of slide 72 under the microscope, and, on the other hand, an assembly composed either of reflecting elements 79 or slits enabling the transmission of a signal using sources of the LED type, said signal being collected by photodiodes (not shown) contained in the casing 76. Due to this assembly, all combinations of movements are thus possible. Finally, it will be noted that the elements could have various configurations but that they simply have to be arranged in accordance with the desired program.

It has been seen that in immunofluorescence it is necessary, on the one hand, to observe and quantify in a very short time period and, on the other hand, never to observe and quantify the same point twice. For example, it could be carried out by sampling. A complete automatic cycle for a slide containing (for example) 10 wells, could be the following:

The starting point being fixed due to the luminous point 78 on the auxiliary plate 74, the device being started up (manually), stage 10 moves and the stage and disc assembly is immobilized from a signal emanated by the upper "opto" 75, which itself is controlled by the reflection on the first edge of the square 79 shown in FIGS. 10 and 11a. Stage 10 being immobilized, such that the first localized zone (field) 80 on slide 72, is located significantly inside cell 80′, focusing will be carried out, either automatically or manually. It will be noted that localized zone 80 on well 80′ is the homolog in position of the luminous point 78 on the visible image 78′ of the auxiliary plate 74.

If the focusing is manual, the operator will send a pulse.

If the focusing is automatic, there will be sent the control pulse for starting the sequences and resetting the counters and the display device 50 to zero. When disc 18 is stopped, it is immobilized due to an optoelectronic device 30 at the outputs of the filter-bearing devices and at the beginning of the black and white analysis sequence (track 29 and disc 18). When it receives the control pulse for starting the sequences, disc 18 starts up, and the stage moves in X. The stage 10 will be again immobilized during the sequential storing or loading in memory of the red, then the green, and will automatically start up again at the end of this operation due to optoelectronic device 30 coming from disc 18. It can be seen that the assembly of image wells, such as 78′, constitutes visualization means for the real wells of slide 72, and that the assembly of elements, such as 79, constitutes stopping and reading control means on localized zones in slide 72, cooperating with the optoelectronic device 30 of disc 18 and the optoelectronic device 75 for the X movements.

In this manner, for example, 10 contiguous or not contiguous samples can be observed and quantified.

After the tenth sample inside well No. 1, the calculator sends a signal which, on the one hand, will interrupt the loading of memory and, on the other hand, will "block" the picture tube 17 until the beginning of the following well where the same cycle will be repeated, and so on for the five wells of the first row. At the end of the first row, the optoelectronic device located inside casing 76, in identifying the end of the X analysis due to the reflecting track 81 on the lower surface of the auxiliary plate 74 (see FIG. 11b), will provide Y movement of the stage to the next lower row, where the X movement cycle will be repeated, for example, in the reverse direction. At the end of this second X movement cycle, the optoelectronic device mentioned above will detect the reflecting track 82 indicating the end of analysis and providing, in cooperation with the reflecting mark 83, the return of slide 72 more or less to its initial position.

It can therefore be seen that the assembly of tracks 81-82 and of the mark 83 constitutes Y movement means, in cooperation with the optoelectronic device 76.

Since the system of the invention enables quantification of the results, a few samples of such are given below. The sampling method has already been mentioned above and, for the convenience of the operation, it has been seen that it was limited to 10 samples. The calculator will therefore record 10 successive values corresponding to the amplitude of the signals, in "peak" or integrated value, after correction, representing the positive part of (V-R) on the one hand, and the positive part of (R-V) on the other hand.

If, for example, titration of toxoplasmosis is carried out by arranging in successive wells dilutions of 1/50, 1/100, 1/200, 1/400, 1/800, 1/1600, 1/3200, 1/6400, etc., of the serum to be studied, the calculator will give an average value of the 10 samples taken in one well and corresponding to one of the dilutions.

Figure 12:
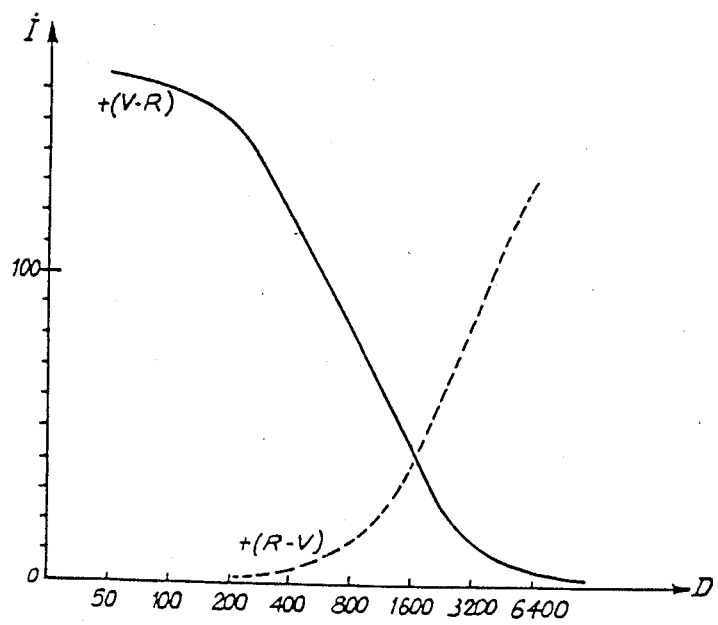
FIG. 12 represents the general shape of the titration curves in an application to toxoplasmosis.

FIG. 12 gives the general shape of curves obtained for a titration where the dilutions are shown by D on a logarithmic scale and the intensities of signals (V-R) and (R-V) are carried by I on a linear scale. On these curves the sharp decreasing of +(V-R) and an increasing +(R-V) will be noted.

It has been noticed that the cross point corresponds more or less to the last positive dilution, a result which itself corresponds to the titer of the serum.

Another quantification process can be necessary for certain applications, for example, the determination of the HLA specificities group, where no titration is carried out. In this case, surface measurements of the elements emitting +(V-R) and +(R-V) are carried out. The calculator can, moreover, determine the ratios of these surfaces to the total field.

Also, dependent upon the circumstances, a combination of the first method for measuring the amplitude and of the second method for measuring surfaces can be used in order to obtain greater reliability of the results.

While the present description of the invention has been made with regard to one particular embodiment, it is clear that many modifications may be made in the details, in particular by substituting technical equivalents for certain devices or functions without departing from the scope of the invention.

What is claimed is:

1. A system for the automatic observation and quantification of phenomena capable of being detected by fluorescence and appearing in a localized zone (8), said system comprising a source of radiation (2), optionally associated with an excitation filter (5), for sending onto said localized zone (8) excitation radiation capable of producing said fluorescence, optical observation means (7) for said localized zone (8), and at least one filter (12) for blocking the excitation radiation and arranged in the path of the luminous fluorescence radiation emanating from said localized zone (8), characterized in that it comprises disc means (18) provided with at least one peripheral indentation (21) and two different colored filters (22, 23) selected in accordance with the wavelength of the luminous fluorescence radiation for examining said localized zone (8), a variable gain picture-taking tube means (17) for successively examining said localized zone (8) through said optical observation means (7) and through said at least two different colored filers (22, 23), memory means $38_R$, $38_V$) for storing the electric signals corresponding to the individual colored images seen by said picture-taking tube means (17), means for simultaneously recovering said electric signals at the output of said memory means, and means for separately adjusting the level of the background for each colored image under the control (by 44) of the amplification gain of said tube means; wherein the signals emanating from said picture-taking tube have a dome-shaped background, and said system is further characterized in that it comprises generator means (45), under the control of the gain of said picture-taking tube means (17) and producing inverted dome-shaped signals (AD), for cancelling the dome-shaped background of the signals emanating from said picture-taking tube means and caused by the fact that the brightness of a luminous area is generally higher at the center of the area than on the boundaries of said area.

2. The system of claim 1, wherein the colored filters comprise at least one red filter (22) and one green filter (23).

3. The system of any one of claims 1 or 2, wherein said picture-taking tube means (17) also directly examines said localized zone (8) in order to give a black and white representation thereof which is used for the focusing of said picture-taking tube means.

4. The system of claim 3, wherein said disc means (18) has opaque parts (24,25,26), and wherein said picture-taking tube means (17) is blocked between two successive examinations through successive colored filters and between an examination through a colored filter and a direct examination for giving the black and white representation by means of said opaque parts so as to allow the residual remanence effect of said picture-taking tube means to become negligible during the corresponding time-rotation of said disc means.

5. The system of claim 4, characterized in that said disc means (18) is also provided with tracks (27,28,29), and means for rotating said disc means so as successively to cause said at least one indentation, colored filters, opaque parts and tracks to intercept the luminous beam of fluorescence (11) sent to said picture-taking tube means (17).

6. The system of claim 5, characterized in that it comprises fixed sensor means (30,31,32) for monitoring said tracks, and wherein the rotating disc means (18) cooperates with said sensor means to synchronize the storing of the signals in said memory means ($38_R$ and $38_V$) and to synchronize the other elements of said system.

7. The system of claim 1, wherein said generator means (45) supplies inverted dome-shaped signals (AD) both in the line direction and in the frame direction.

8. The system of claim 7, characterized in that, downstream of said memory means ($38_R$ and $38_V$), it comprises means ($46_R$ and $46_V$) for background cancellation using integration and rectification of the image signals and subtraction of the signals thus obtained from the real signals.

9. The system of claim 1, characterized in that it comprises means (47,48) for producing, on the one hand, the difference R-V between the signals emanating from a first colored filter (22) and those emanating from the second colored filter (23) and, on the other hand, the difference V-R between the signals emanating from the second colored filter (23) and those emanating from the first colored filter (22).

10. The system of claim 9, characterized in that, downstream of said memory means ($38_R$ and $38_V$), it comprises means ($46_R$ and $46_V$) for background suppression using integration and rectification of the image signals and subtraction of the signals thus obtained from the real signals.

11. The system of claim 1 or 10, characterized in that, downstream of said memory means ($38_R$ and $38_V$), it comprises artifact suppression means for enabling the suppression of each artifact by means of a portion of itself.

12. The system of claim 1, characterized in that it comprises automatic mechanisms enabling the movement of stage 10 in a focusing plane relative to objective lens 7, including, on the one hand, visualization means (78') of the real cells of a slide (72) and stopping and reading control means (79) on the localized zones (80) of the slide (72), cooperating with an optoelectronic device (30) of disc (18) and with another optoelectronic device (75), for the X movements and, on the other hand, control means (81, 82 and 83), cooperating with still another optoelectronic device (76), for the Y movements.

13. The system of claim 1 further comprising means (41 to 44) for varying the gain of said picture-taking tube means (17) such that the amplitude of the output signals therefrom is always greater than a threshold beneath which the remanence of tube means (17) becomes detrimental.

* * * * *